United States Patent [19]

Litovitz

[11] Patent Number: 5,968,527
[45] Date of Patent: Oct. 19, 1999

[54] PROTECTION OF LIVING SYSTEMS FROM THE ADVERSE EFFECTS OF STRESS

[75] Inventor: Theodore A. Litovitz, Annapolis, Md.

[73] Assignee: Catholic University of America, The, Washington, D.C.

[21] Appl. No.: 08/984,885

[22] Filed: Dec. 4, 1997

Related U.S. Application Data

[60] Provisional application No. 60/038,042, Feb. 27, 1997, and provisional application No. 60/040,045, Mar. 7, 1997.

[51] Int. Cl.$^6$ .......................................................... A61K 9/00
[52] U.S. Cl. ............................. 424/400; 424/1.11; 424/9.3; 424/9.322; 424/422
[58] Field of Search ................................... 424/1.11, 9.3, 424/9.322, 400, 422

[56] References Cited

U.S. PATENT DOCUMENTS

| | | | |
|---|---|---|---|
| 3,566,877 | 3/1971 | Smith | 128/422 |
| 3,890,953 | 6/1975 | Kraus | 128/1.5 |
| 3,893,462 | 7/1975 | Manning | 128/421 |
| 3,911,930 | 10/1975 | Hagfors | 128/421 |
| 3,952,751 | 4/1976 | Yarger | 128/422 |
| 4,105,017 | 8/1978 | Ryaby | 128/1.5 |
| 4,266,532 | 5/1981 | Ryaby | 128/1.5 |
| 4,315,503 | 2/1982 | Ryaby | 125/1.5 |
| 4,428,366 | 1/1984 | Findl | 128/1.5 |
| 4,459,988 | 7/1984 | Dugot | 128/419.7 |

(List continued on next page.)

OTHER PUBLICATIONS

Heart and Stroke Facts, American Heart Association National Center, 1996, p. 1.

Bonventre JV, Mediators of Ischemic Renal Injury, Ann. Rev. Med 39, 1988, p. 531–544.

Ananthan J, Goldberg Al, Voelmy R, Abnormal Proteins Serve As Eukaryotic Stress Signals and Trigger the Activation of health shock Genes, Science 232, 1986, pp. 552–524.

Mestril r, Dillmann WH, Heat Shock Proteins and Protection Against Myocardial Ischemia, J Mol Cardiol 27, 1995, pp. 45–52.

Donnelly TJ, Sievers RE, Visem FLJ, Welch WJ, Wolfe CL, Heat Shock Protein Induction in Rat Hearts, Circulation 85, 1992, pp. 769–778.

Walker DM, Pasini E, Kucukogolu S, Lin JJC, Feramisco JR, Heat Stress Limits Infarct Size in the Isolated Perfused Rabbit Heart, Cardiovasc Res 27, 1993, pp. 962–967.

Li GC, Mak JY, Induction of heat shock protein synthesis in murine tumors during the development of thermotolerance, Cancer Res 45, 1985, pp. 3816–3824.

Iwaki K, Chi SH, Dillman WH, Mestril R, Induction of HSP70 in cultured rat neonatal cardiomyocytes by hypoxia and metabolic stress, Circulation 87, 1993, pp. 2023–2032.

Hutter MM, Sievers RE, Barbosa V, Wolfe CL, Heat shock protein induction in rat hearts: a direct correlation between the amount of heat shock protein induced and the degree of myocardial protection, Circulation 89, 1994, pp. 355–360.

Mestril RM, Chi SH, Sayen MR, O'Reilly K, Dilllman WH, Expression of inducible stress portein in rat heart myogenic cells confers protection against simulated ischemia induced injury, J Clin Invest 93, 1994, pp. 759–769.

(List continued on next page.)

*Primary Examiner*—Jose' G. Dees
*Assistant Examiner*—Kathryne E. Shelborne
*Attorney, Agent, or Firm*—Pillsbury Madison & Sutro

[57] ABSTRACT

Methods and apparatus are described to inhibit the adverse health effects of ischemia, hypoxia, anoxia or other stress by the application of a time-varying field to the region of the affected organ(s) for a short period of time (of the order of 20 minutes). A "field" means a time varying electric field, a time varying magnetic field and/or a radiating electromagnetic field. The exposure can be started up to two or more hours in advance of the ischemic event or other stress causing event. Inhibition occurs even if the field is applied after the onset of ischemic or anoxic stress.

4 Claims, 3 Drawing Sheets

U.S. PATENT DOCUMENTS

| | | | |
|---|---|---|---|
| 4,535,775 | 8/1985 | Brighton | 128/419.7 |
| 4,548,208 | 10/1985 | Niemi | 128/419.7 |
| 4,561,426 | 12/1985 | Stewart | 128/1.5 |
| 4,600,010 | 7/1986 | Dugot | 128/419.7 |
| 4,616,629 | 10/1986 | Moore | 128/1.5 |
| 4,622,952 | 11/1986 | Gordon | 128/1.3 |
| 4,622,953 | 11/1986 | Gordon | 128/1.3 |
| 4,654,574 | 3/1987 | Thaler | 320/14 |
| 4,683,873 | 8/1987 | Cadossi | 128/1.5 |
| 4,757,804 | 7/1988 | Griffith | 128/1.5 |
| 4,794,928 | 1/1989 | Kletschka | 128/344 |
| 4,798,824 | 1/1989 | Belzer | 514/60 |
| 4,838,269 | 6/1989 | Robinson | 128/344 |
| 4,873,230 | 10/1989 | Belzer | 514/60 |
| 4,879,283 | 11/1989 | Belzer | 514/60 |
| 4,920,044 | 4/1990 | Bretan, Jr. | 435/1 |
| 4,932,951 | 6/1990 | Liboff | 600/13 |
| 5,123,898 | 6/1992 | Liboff | 600/13 |
| 5,131,904 | 7/1992 | Markoll | 600/14 |
| 5,224,922 | 7/1993 | Kurtz | 600/13 |
| 5,269,746 | 12/1993 | Jacobson | 600/13 |
| 5,330,410 | 7/1994 | Baylink | 600/13 |
| 5,338,286 | 8/1994 | Abbott | 600/14 |
| 5,348,945 | 9/1994 | Berberian | 514/21 |
| 5,366,435 | 11/1994 | Jacobson | 600/13 |
| 5,387,176 | 2/1995 | Markoll | 600/14 |
| 5,441,495 | 8/1995 | Liboff | 600/9 |
| 5,453,073 | 9/1995 | Markoll | 600/14 |
| 5,518,496 | 5/1996 | McLeod | 600/14 |

OTHER PUBLICATIONS

Heads RJ, Yellon DM, Latchman DS, Differential cytoprotection against heat stress or hypoxia following expression of specific stress protein genes in myogenic cells, J Mol Cell Cardiol 27, 1995, pp. 1669–1678.

Joannidis M, Cantley LG, Spokes K, Medina R, Pullman J, Rosen, Epstein FH, Induction of heat shock proteins does not prevent renal tubular injury following ischemia, Kidney Int.

Marber M, Mestril R, Chi SH, Sayen MR et al. Overexpression of the rat inducible 70–kD heat stress protein in a transgenic mouse increases the resistance of the heart to ischemic injury, J Clin Invest. 95, 1995, pp. 1446–1456.

McLeod KJ, Lee RC, Ehrlich HP, Frequency dependence of electric field modulation of fibroblast protein synthesis, Science Jun. 12; 236(4807), 1987, pp. 1465–1469.

Goodman R, Henderson A, Patterns of transcription and translation in cells exposed to EM fields: A review. Mechanistic Approaches to Interactions of Electric and Electromagnetic Fields with Living Systems, Ed Martin Blank and Eugene Pindl, Plenum Publishing Corp.. 1987, pp. 217–230.

Goodman R, Henderson AS, Exposure of salivary gland cells to low–frequency electromagnetic fields alters polypeptide synthesis. Proc Natl Acad Sci USA Jun; 85(11), 1988, pp.3928–3932.

Blank M, Goodman R, An electrochemical model for the stimulation of biosynthesis by external electric fields, Bioelectrochem and Bioenerg. 19, 1998, pp. 569–580.

Albertini A, Noera G, Pierangeli A, Zucchini P, Cadossi R, Effect of low–frequency pulsed electromagnetic fields on experimental myocardial infarcts in rats, Electromagnetics in.

Edgington SM, Therapeutic applications of Heat Shock Proteins, Biotechnology 13, 1995, pp. 1442–1444.

Sedlak BJ, Heat Shock proteins finding a broad range of clinical uses and applications, Genetic Eng. News 17(3), 1966, p. 6.

Lee BS, Chen J, Angelidis C, Jurivich DA, Morimoto RI, Pharmacological modulation of heat shock factor by anti––inflammatory drugs results in protection against stress–induced cellular damage, Proc Natl Acad Sci USA, Aug 92(16), 1995, pp. 7202–7211.

Chapter 9, Biomagnetic Effects, a part of NMR Imaging in Biomedicine, Mansfield et al., Academic Press, Apr. 13, 1982, pp. 297–310.

Liboff, AR, Cyclotron Resonance in Membrane Transport, a part of Interactions Between Electromagnetic Fields and Cells, Chiabrerra et al., Plenum Publishing, 1985, pp. 281–296.

PROTECTION OF LIVING SYSTEMS FROM THE ADVERSE EFFECTS OF STRESS

RELATED APPLICATIONS

This application includes material described in Provisional Applications 60/038,042 filed Feb. 27, 1997 and 60/040,045 filed Mar. 7, 1997, and is entitled to the benefits of the filing dates thereof.

FIELD OF THE INVENTIONS

The inventions described herein relate in general to arrangements (apparatus and methods) for protecting living systems from the adverse effects upon them of ischemia, anoxia, hypoxia (a lack of sufficient oxygen), reperfusion and other environmental stresses. More specifically, the inventions are directed to methods and electrical, electronic, and electromagnetic devices, systems and installations and their effect on humans, animals, and other living systems comprising cells. The inventions limit the damage to living cells caused by any condition which stresses the cells, such as limits on the availability of oxygen to these cells. The methods may be employed in the combating of damage due to toxic chemicals such as used in chemotherapy, ionizing radiation (such as ultraviolet light, gamma rays or beta rays), atherosclerosis, restenosis after angioplasty, and nerve damage in human or animal subjects in need of such treatment. The inventions involve applying certain electric, magnetic or radiating electromagnetic fields for the purpose of activating endogenous protective mechanisms used by the cells to limit the deleterious effects such as those caused by ischemia, reperfusion, athersclerosis, ionizing radiation, toxic chemicals or other stress.

DESCRIPTION OF RELATED ART

When myocardial infarcts occur, loss of functional myocardium still persists despite numerous interventions available to achieve myocardial reperfusion. This loss of functional myocardium can lead to subsequent severe cardiac failure and represents a significant medical problem[1]. (Citations of numbered footnotes appear at the end of this specification.) Even when severe cardiac failure does not occur the salvage of additional myocardium is highly desirable to allow for a fuller more active life following a myocardial infarction. Similarly following ischemia to the brain (e.g. stroke) rapid reversal or limitation of extent of injury will lead to superior neurological outcomes.

A number of changes within cells are produced by ischemia, hypoxia, or anoxia[2]. These changes in cellular function represent a form of metabolic or hypoxic stress which is known to produce protein denaturation. A similar increase in protein denaturation within the cell has been reported to result in the onset of the heat shock response which increases the synthesis of the so-called heat shock proteins[3], now often called stress proteins. The heat shock response has been shown to occur in all organisms examined to date following an elevation in temperature. The response to this stress is an increase in the synthesis of the family of proteins collectively known as heat shock proteins (HSPs) of varying molecular weights. For example HSP70 is one member of the family whose molecular weight is 70 kilodaltons. Its inducible form is sometimes called HSP70i or HSP72. Below in this document when I refer to HSP70 I mean the inducible form. Although first discovered following an elevation in temperature it is now recognized that the heat shock response is typical of the response to many stresses on the cell. These include but are not limited to the stress caused by ischemia, anoxia, hypoxia, reperfusion, hypoglycemia, hypotonicity, glucose deprivation and exposure to toxins or ionizing radiation and infections.

In response to stress, cells synthesize the family of proteins known as HSPs. The HSPs help the cell survive by assisting damaged cells with repair and protecting them against further harm. They also help fold and transport proteins. HSPs ensure that the folding and assembly of enzymes and other proteins occurs rapidly and correctly. This response causes a transient rearrangement of cellular activities to cope with the stress period by protecting essential components within the cell so as to permit it to resume normal activity during recovery from the stress. This ability of a cell to provide endogenous processes for self preservation has attracted the attention of many investigators searching for ways to salvage myocardium. In particular the phenomenon of "cross protection" has been investigated. "Cross protection" or "cross tolerance" are terms which describes the use of a non-lethal application of one stress (e.g. heat) to protect against the deleterious effects of another stress (e.g. anoxia). This technique has been applied as a means of protecting cardiac myocytes against ischemia-induced injury[4]. Several studies have shown that a hyperthermic treatment of experimental animals can result in a significantly improved myocardial salvage following coronary occlusion and reperfusion in vivo in animals[5] as well as in an isolated perfused heart model[6].

The protective nature of HSPs is documented by the observation that a mild heat shock (42° C.) confers resistance to the cell against a subsequent, normally lethal, heat shock (45° C.).[7] The synthesis and degradation of HSPs precedes the development and decline, respectively, of thermotolerance. This fact has been taken as evidence that these proteins are involved in the development of thermotolerance. Cardiomyocytes respond to hypoxia and metabolic stress with increased HSP70 production which points to a protective role of HSPs during ischemia/reperfusion injury.[8] The protective role of HSPs was confirmed by Currie and co-workers. They found that isolated perfused hearts from rats which had received a 15 min heat treatment at 42 C 24 hours previously exhibited an improved contractile recovery after a 30 min period of low-flow ischemia followed by reperfusion as compared to hearts from non-heat treated animals. Obviously, whole body or whole organ heat stress results in many cellular changes besides an increase in the expression of HSPs that could be responsible for the observed protection against ischemia. Nonetheless, recent studies have shown that HSPs and, in particular, the amount of HSP70 present following a whole body heat shock is directly related to the degree of myocardial protection obtained.[9] Further direct evidence that HSP70 is able to cross-protect against ischemic injury has recently been obtained using myogenic cell lines. It was found that when myogenic cells that had previously received a mild heat shock were submitted to conditions mimicking ischemia in vitro (hypoxia, glucose deprivation, hypotonicity, or simulated ischemia, these cells were better able to survive than the cells which had not previously been heat shocked).[10]

It must be emphasized at this point that application of a stress and the resultant production of stress proteins does not guarantee cross-protection from another type of stress. When this cross-protection does not occur it is described as differential cytoprotection. One example of differential cytoprotection has been demonstrated by Heads et al.[11] who showed that rat heart cells respond to sub-lethal heat stress by preferential synthesis and accumulation of several members of functionally and compartmentally distinct families of heat shock (or stress) proteins (such as HSP70, HSP90, HSP60 and HSP27). Some of these have been implicated in the development of thermotolerance and resistance to other environmental stresses. It is unclear which members of this family of heat shock proteins are crucial in anoxia protection and which are crucial in thermotolerance. Heads et al found that HSP70i was able to provide a high level of protection against both thermal stress and hypoxia stress. However, although HSP90b and HSP60 were able to protect against thermal stress they were not capable of protecting against hypoxia. This differential cytoprotection was also demonstrated by Joannidis et al[12] who showed that induction of heat-shock proteins (via hyperthermia) did not prevent renal tubular injury following ischemia.

Since 1986 Wolfgang Dillmann and his group at the University of California in San Diego have worked to demonstrate the role of HSPs in protecting cells from much of the ischemia-related damage which occurs. Recently this group has published an impressive proof of the role of HSPs.[13] In this report hearts harvested from transgenic mice that overexpressed HSP70 suffered 40–50% less damage than normal hearts when subjected to ischemic injury. They also report similar protective effects appear when transgenic mice are subjected to a laboratory model of brain ischemia that is meant to mimic stroke.

At this time there appear to be two strategies for implementing the possible protective role of HSPs when applied to humans. (Note: elevating the temperature of the organ or whole body does not seem to be a feasible approach). The first would be gene therapy to selectively deliver HSPs to target organs for individuals at high risk of ischemia injury to an organ who are diagnosed as needing a surgical procedure such as a heart bypass operation. Of course the problem here is whether or not one can deliver enough HSP without side effects. The second method would employ a pharmocologic approach by developing drugs that induce the endogenous HSP gene. However, because HSPs are normally induced by rather toxic compounds, the challenge is to develop drugs that turn the gene on selectively without poisoning the cell.

The ability of an electric current to modulate protein synthesis was shown by McLeod et al.[14] as early as 1987. However in this work the types of protein synthesized were never determined and no evidence of the stimulation of heat shock proteins was presented. In 1987 and 1988 Goodman and Henderson[15, 16] showed that extremely low-frequency magnetic fields can cause measurable changes in protein synthesis. However, they reported that the pattern of polypeptide synthesis differed from that seen with heat shock. They stated that although changes in protein synthetic patterns occur in response to low frequency magnetic fields only a portion of these changes overlap those expected from exposure of cells to thermal shock. They found that although there are similar (or the same) protein groups in heat-shocked cells and cells exposed to the fields, the overall patterns and number of polypeptides resolved are different for the two different stimuli. Thus the above protein synthesis papers do not suggest in any way that the proper protective stress proteins are being produced either by electric or magnetic fields. In 1988 Blank and Goodman reported an analysis of the of synthesis of proteins induced by electromagnetic fields[17] in salivary glands of Sciara. They reported that the protein synthesis modifications caused by heat shock (HS) and by electromagnetic (EM) stimulation had certain similarities. However they noted a significant difference in the effects of HS and EM stimulation on protein synthesis. They found that electromagnetic (EM) fields caused an increased synthesis of proteins in the molecular weight range 20–50 kD but they discovered a generally reduced synthesis of polypeptides in the 50–90 kD molecular weight range. As described above (ref 9) the degree of myocardial protection induced by heat shock is directly related to the amount of HSP70 (a 70 kD polypeptide) induced by a stimulus or stress. But Blank and Goodman report that the synthesis of HSP70 is either reduced by EM fields or only a negligible (2%) increase occurs under certain signal conditions. They found that a much larger (50%) increase in HSP70 is caused by heat shock. Thus Blank and Goodman teach away from my inventions since their data suggest that time varying magnetic fields would either have no effect on or reduce the endogenous protection against myocardial damage due to ischemia and reperfusion. I have discovered that certain fields can protect against ischemia/reperfusion damage. I do not know whether or not the mechanism by which the field protects against ischemia/reperfusion is related solely, to heat shock proteins. It could be a combination of induced effects and other effects on cell function.

In U.S. Pat. No. 5,441,495 Liboff et. al. describe an electromagnetic treatment therapy for stroke victims. The technique they teach is expensive, complicated and could never be self-administered by an untrained individual. The method utilizes a special interaction known as cyclotron resonance. Only certain well defined frequencies can be used. The earth's magnetic field must be canceled out with special coils containing currents determined by sophisticated sensors. A new DC field must be generated, which DC field must be specially aligned along a predetermined axis through the patient's cerebral tissue. The AC magnetic fields proposed (of the order of (~) 0.1 mG) are much lower than the minimum required by my invention. The magnetic fields must be very uniform through out the tissue to be treated. This significantly increases the complexity and expense of the equipment needed to apply the prescribed magnetic field. In addition the wave forms of the current in the coils must contain a DC component. These conditions which are necessary for the cyclotron resonance condition are sophisticated and take time to set up. None of these conditions are necessary in my invention. The above apparatus could never be inexpensive enough to be made available in the homes of people who are possible candidates for a heart attack. Nor can they be used as a self administered treatment modality.

A number of patents and other prior art also teach the cyclotron resonance technique to promote healing. I describe some of these below. They all suffer from the disadvantages described above. They include U.S. Pat. No. 5,330,410 which utilizes the cyclotron resonance to stimulate growth factor. Again, this is a method for repair and healing as opposed to prevention of damage. In U.S. Pat. No. 5,518,496 McLeod et al propose a special coil to use the complicated resonance technique for regulating growth of living tissue. This coil is designed to be used every day for many weeks to aid in healing. Kurtz in U.S. Pat. No. 5,224,922 combines a time varying field with a DC field as in cyclotron resonance to produce regenerative effects.

A number of patents and other prior art teach that healing of bone and other tissues can be enhanced by the use of pulsating electromagnetic fields with very special pulse shapes. For example, in U.S. Pat. No. 4,683,873 Cadossi et al describe a method for treating living tissues, especially bone fractures, by using magnetic pulses which have a wave form which comprised of three segments in chronological order which are composed of a positive segment, followed by a negative segment whose peak value is less than the positive peak in the first portion. The duration of said positive portion must be between 1 and 3 milliseconds. Cadossi teaches that if the special pulse conditions are not met then beneficial healing will not occur. He further teaches that the treatment must be applied for between 8 and 14 hours per day whereas in my invention a single exposure of ~20 minutes is used. Again this particular prior art deals with healing not prevention of damage. Finally their equipment could not be self administered and is too expensive to have available in every home.

Cadossi et al apply the same well defined pulse shape described above in the treatment of myocardial infarcts in rats[18]. They teach that very large pulsed magnetic fields must be used for very long times (30 Gauss peak lasting for 18 hours). They teach that this treatment helps only in permanent occlusion and does not help prevent reperfusion damage.

In U.S. Pat. Nos. 5,131,904, 5,453,073, and 5,387,176 Markoll proposes to heal arthritic conditions, diseased organs, and sports type injuries using a special rectangular pulsed waveform at the rate of 1–30 Hz. The field here is of the order of 12.5 Gauss and 18 treatments were used.

In U.S. Pat. No. 5,269,746 Jacobson teaches that sinusoidal waveforms can be used for the treatment of mammals for epilepsy and Parkinson's disease. He proposes specific frequencies between 5.3 to 9.8 Hz and between 197 to 247 Hz. In U.S. Pat. No. 5,366,435 he teaches that viruses and genetic diseases can be treated with similar fields. In addition Jacobson proposes that patients must be exposed over extended periods of time using magnetic fields whose strength lies between 0.35 and 0.7 mG.

In U.S. Pat. No. 5,338,286 Abbott teaches that bone growth stimulation can be achieved by selective spectral suppression in the pulsed electromagnetic field. This as in the prior art described above uses sophisticated variations in pulse shape and duration to improve the healing properties of a field. Abbott does not address the question of prevention of damage.

In U.S. Pat. No. 5,348,945 Berberian, Tytell and Gower (citing many references) describe a method of combating mortality in a cell or tissue under stress. The method comprises contacting HSP70 to the cell or tissue in an amount effective to enhance the survival of that cell or tissue. The method may be employed in the combating of atherosclerosis, restenosis after angioplasty, and nerve damage in human or animal subjects in need of such treatment. A pharmaceutical composition comprising a therapeutically effective amount of HSP 70 in a pharmaceutically acceptable formulation is also disclosed.

The conclusions reached in the above publications on electromagnetic stimulation of protein synthesis help explain why in the years since 1990 (even though there has been enormous interest and a furious effort to develop means of generating and introducing protective stress proteins) no one has discovered that simulation of stress proteins can be useful for conferring protection against ischemia/reperfusion. The great activity in the therapeutic applications of HSPs has been summarized in two articles[19, 20] New companies have been formed which deal only in the production and application of HSPs. A new journal entitled *Cell Stress & Chaperones* and completely devoted to research and applications of HSPs is now being published. The range of applications for HSPs being developed is remarkable. They include uses as immune modulators, curing patients of existing tumors, protecting against specific cancers, HSP-based vaccines, and the treatment of ischemia caused by heart attack or stroke.

SUMMARY OF INVENTIONS

It is the purpose of my inventions to protect cells, tissues, and organs from the deleterious effects of the stresses listed above. This is done by using time-varying fields, i.e., magnetic fields, electric fields and electromagnetic fields which can be applied in a localized or systemic manner. None of the above authors or anyone else before me to my knowledge has discovered the use of such fields, nor simple, inexpensive, self administered methods of using such fields, to stress the cells in such a way as to stimulate the endogenous biological defense mechanisms and thus offer cross protection against the harmful effects of ischemia, anoxia, hypoxia, metabolic stresses, toxic chemicals, ionizing radiation and other stresses. The essential purpose here is to prevent cell death rather than to heal injury.

Thus I find that despite the considerable activity in the field of stress proteins and despite an active search for non-toxic ways of introducing stress proteins into biological systems, no one has developed my simple, inexpensive methods, which utilize time varying fields of the aforesaid types to confer cross protection against ischemia/reperfusion injury.

As noted above, there is a significant amount of prior art which suggests the use of electromagnetic, electric or magnetic fields for the purpose of healing living tissue. In all of these the stimulus is used for healing damage which has already occurred (e.g. healing of fractured bone, wound healing, and treating inflammation). None of these teach how by using short duration electromagnetic field exposures generated by simple, inexpensive equipment one can prevent damage to living tissue which would usually be caused by a stress such as ischemia/reperfusion.

OBJECTS OF INVENTIONS a) To create simple inexpensive methods and devices to limit damage due to an ischemic event and which could be available at all times in every home, office, and hospital room and could be utilized and self-administered by any individual at the first symptoms of a heart attack or stroke.

b) To create simple inexpensive methods and devices which could be portable for use away from the home or office.

c) To create simple inexpensive methods and devices to limit damage due to an ischemic event which could be worn by any one with a risk of myocardial infarction or stroke and could be activated at the first sign of symptoms of a heart attack or stroke.

d) To create simple inexpensive methods and devices to limit damage due to an ischemic event (e.g., angina attack) which could be used previous to and in anticipation of an ischemic event which would could prevent damage due to the event.

e) To create simple inexpensive methods and devices which would could be used by a physician as a pre-operative procedure to confer protection to vital organs from a reduction in blood supply during a surgical procedure or by any procedure which can stress the organs of the body.

f) To create simple inexpensive methods and devices to combat mortality in a cell under stress. The methods comprise inducing heat shock proteins by applying a magnetic field whose magnitude and time duration are appropriate to effectively enhance the survival of that cell.

g) To create simple inexpensive methods and devices to combat mortality in a tissue under stress, such as arterial tissue. The method comprises inducing heat shock proteins by applying a magnetic field whose magnitude and duration are appropriate to effectively enhance the survival of the cells residing in that tissue. The tissue may be treated in vivo or in vitro. Among other things, these methods are useful for preserving organs for transplant.

h) To create simple inexpensive methods and devices for combating atherosclerosis in a human or animal subject in need of such treatment. The methods comprise inducing heat shock proteins in the subject by applying a magnetic field whose magnitude and time duration is appropriate to reduce necrosis in arterial plaques residing in the subject.

i) To create simple inexpensive methods and devices for combating arterial restenosis after angioplasty in a human or animal subject in need of such treatment comprising administering to arterial tissue residing in the subject in need of such treatment a magnetic field whose strength and duration are appropriate to combat restenosis.

j) To create simple inexpensive methods and devices for combating nerve damage in a human or animal subject in need of such treatment, comprising applying a magnetic field whose magnitude and duration are appropriate to effectively enhance the survival of nerve cells under stress.

k) To create a simple and inexpensive method and device for protecting normal tissue from the effects of ionizing radiation particularly when this radiation is applied to treat malignant tissue.

l) To create a simple and inexpensive method and device for protecting normal tissue from toxic chemicals, particularly those used in chemotherapy to treat malignant tissue.

DRAWINGS

This application includes certain drawings referred to hereinafter. Briefly stated, in these:

DETAILED DESCRIPTION OF INVENTIONS

Figure 1:
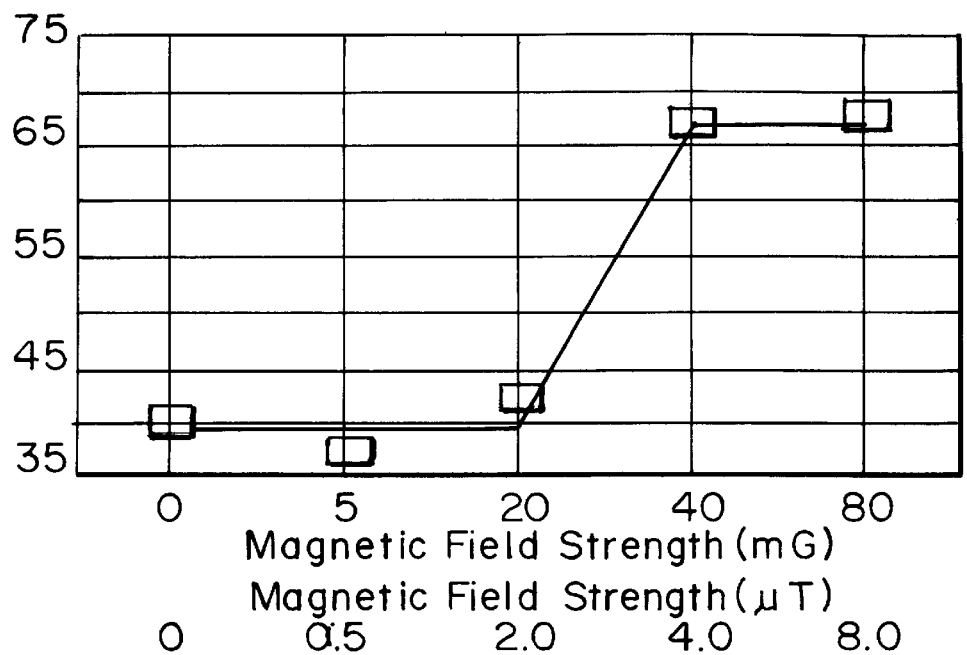
FIG. 1 shows the effect of changing the rms amplitude of a 60 Hz magnetic field on chick embryos.

I have discovered that the adverse health effects of ischemia, hypoxia, anoxia or other stress may be strongly inhibited by the application of a time-varying field to the region of the affected organs(s) for a short period of time (of the order of 20 minutes). I refer herein to a "field" to mean a time varying electric field, a time varying magnetic field and/or a radiating electromagnetic field. I have discovered that this exposure can be started up to two or more hours in advance of the ischemic event or other stress causing event. In addition I have found that inhibition of ischemic effects occur even if the field is applied after the onset of ischemic or anoxic stress. Preferably the field should be applied as soon as possible after the ischemic event begins and before reperfusion occurs. This is because the object of the methods described in this application is mainly to prevent rather than heal damage due to ischemia and subsequent reperfusion. When a time varying magnetic field is applied its magnitude preferably be should be in the range 4 to 10 $\mu$T. Below 4 $\mu$T the effectiveness of the magnetic field drops rapidly. For example application of a 60 Hz sinusoid at 2 $\mu$T and below yields no beneficial effect. Above 10 $\mu$T needless power is consumed. Preferable frequencies lie above 30 Hz. Power line frequencies of 50 or 60 Hz are quite useful because they yield highly beneficial results and the fields can be generated using very inexpensive components. Frequencies as high as 6000 Hz and above are still quite effective. It is important to note that I have discovered that the fields do not have to be uniform across the organ to be treated. The main condition on amplitude is that it preferably be above 4 $\mu$T everywhere in the tissue to be protected. This discovery of the great tolerance for non-uniformity of field amplitude has important economic benefits since it allow for the use of simple devices (such as a single coil rather than a double coil) which can be cheaply produced and easily self-administered by a patient. Fields as high as 100 $\mu$T or more are effective. Non-sinusoidal wave forms can be used but they offer no advantage. The preferable pulse repetition rates for pulses are above 30 Hz. If an electric field is directly applied, the preferable range of frequencies is 15 to 100 Hz. The magnitude of the electric field (at the affected organ) should preferably be greater than 1 mv/cm if the frequency of the field is in the range 15 to 100 Hz. For frequencies higher than this the minimum fields needed will be larger (significantly increasing with increasing frequency). When an electromagnetic wave, radio frequency (RF) or microwave, is radiated onto the organ to be protected (e.g. the heart) the minimum field intensity should preferably be about 10 to 50 mW/cm$^2$ and preferably should be amplitude modulated at frequencies in the range 30 to 100 Hz. Pulse modulated waves are not as effective as sinusoidally amplitude modulated ones. Frequency modulated RF energy will not be as effective in protecting against ischemic damage. No measurable rise in temperature is needed or wanted. My inventions do not utilize the heating effects of electromagnetic fields. In all of the fields described above the amplitude and wave form should not fluctuate over time scales shorter than about 10 seconds. Thus even though the exposure time is of the order of 20 minutes or longer, during this exposure time the field parameters (amplitude, waveform, frequency, etc.) may vary but should be constant for intervals of about ten seconds or greater. For example the rms amplitude should not vary by more than about 10% during any 10 second time period. If the field parameters vary on time scales of the order of one second or less the beneficial effects will not occur or be much reduced. If the field parameters are allowed to vary in a random fashion on times scales of 1 second beneficial effects will be reduced.

I have discovered the use of a one time, short, (of the order of 20 minutes) exposure to a time varying magnetic field with no added DC field can prevent damage and avoid the necessity for a electromagnetic field healing therapy. Even greater protection for longer times can be obtained by restimulating for 20 minutes, one to two hours after the end of the first 20-minute treatment. I have also discovered that small fields (of the order of 10$^{-1}$ Gauss) for much shorter times (less than 1 hour) with simple waveforms (sinusoids) can be used to prevent the damage due to ischemia/reperfusion even when there is no permanent occlusion. The simpler waveforms of my inventions offer great economic advantage since the generation of 50 or 60 Hz sinusoids is quite trivial when the power frequency is 50 or 60 Hz (e.g.

in Europe or in the USA). My discovery that weak low frequency fields can be used for short time durations means much less power is needed and the equipment again can be cheaper and made portable at less cost.

I have discovered that to prevent damage due to anoxic and other stresses pulses are not needed, and the magnetic fields should preferably be about 1000 times smaller than that taught by Markoll. I have also discovered that a single short time. exposure (less than 1 hour) of fields above 40 mG are useful and that frequency ranges from 15 to 10,000 Hz are quite effective in preventing organ damage.

Cells of any origin may be treated by the methods of the present invention, including animal, plant, and bacterial cells. Cells may be treated in vitro or in vivo. Likewise, tissues of any origin, including animal and plant tissue, may be treated by the methods of the present inventions either in vitro or in vivo. Animal cells and tissues are preferred for carrying out the present inventions, with mammalian (e.g., dog, cat, human) cells and tissue particularly preferred. The term "animal" as used herein, refers to the subjects of veterinary medicine, such as dog, cat, cow, pig, and horse.

Cells and tissue which are under stress are treated with a magnetic field to combat mortality. For example, cells which are maintained in culture (e.g., for the purpose of producing proteins or other materials from the cells) or tissue which is maintained in culture (e.g., complete organs such as heart, lung, liver or kidney prior to transplant) may be considered as "under stress" for the purpose of practicing the present invention. For example, organs could be placed in a sinusoidal time varying magnetic field for the appropriate exposure time and heat shock proteins would be produced in the organs, making them more resistant to the lack of blood, nutrients and other needed substances that exists once they are removed from the body. The magnetic field could be used in conjunction with placing the organ in known preservation solutions and used in accordance with procedures known to those skilled in the art for these purposes. Such solutions and procedures are disclosed in U.S. Pat. No. 4,920,044, titled "Intracellular Flush Solution for Preserving Organs", U.S. Pat. No. 4,879,283 titled "Solutions for the Preservation of Organs", U.S. Pat. No. 4,873,230 titled "Composition for the Preservation of Organs", and U.S. Pat. No. 4,798,824 titled "Perfusate for the Preservation of Organs". Applicant intends the disclosures of these and all other patents cited herein to be incorporated herein by reference.

Tissue under stress in vivo may also be treated by electromagnetically inducing HSP70 and other stress proteins. For example, arterial and myocardial tissue may be treated by applying time-varying a magnetic field before by-pass surgery to enhance the survivability of cells in that tissue. Cardiac ischemia may be treated by applying a time-varying magnetic field just after or before the time of myocardial infarction to enhance the survivability of cells in those tissues. The kidney may be protected from damage from toxic substances such as the antibiotic Gentamicin by the application of a magnetic field. Arterial tissue may be protected during laser angioplasty and atherectomy by application of a time-varying magnetic field to reduce damage to these tissues arising from such procedures. Nerve tissue (i.e., peripheral nerve and central nerve) which is under stress in vivo may also be treated by the method of the present invention. For example, peripheral nerves which are severed are subject to retrograde degeneration, which degeneration may culminate in death of the nerve cell, or soma, if too great a portion of the nerve's axon is distal to the site of the cut. If degeneration does not culminate in cell death, then an opportunity exists for the nerve to regenerate. Thus, magnetic fields, whose strength and durations are designed to maximize production of HSPs may be applied to such nerve tissue to combat cell mortality which may result from the severing of the peripheral nerve.

Nerve tissue may also be subject to anoxic stress in vivo. For example, anoxic stress may arise from a stroke or burst aneurism which damages nerve tissue by depriving the tissue of blood. When central nerve tissue is so damaged, the damage typically occurs in a watershed pattern in relation to the blood vessels: tissue closest the damaged supply vessel is most severely damaged; tissue furthest from the damaged vessel which is supplied by other vessels is least severely damaged; tissue intermediate of these extremes shows intermediate damage. The affected regions of afflicted subjects are exposed to a magnetic field to combat mortality in cells subject to this type of stress.

As noted above, the present inventions may be employed to combat restenosis after angioplasty. Angioplasty is a procedure for dilating arteries which are occluded or blocked. In a typical transluminal balloon angioplasty procedure, a catheter which carries an inflatable dilation balloon at the distal end is employed to reshape a partially occluded artery. The balloon is inserted in the deflated condition in the restricted portion of the artery and inflated so that the occluded lumen is reshaped by the dilation balloon to allow better passage of blood. The obstructing material is neither dislocated nor removed from the vessel, but rather pressed against the wall. The wall, in turn, is stretched to accommodate the previously obstructing material. After the lumen has been reshaped, the dilation balloon is deflated and removed. The site of the formed obstruction may, however, become reoccluded when/if the vessel returns to its previous configuration: a phenomenon known as "restenosis." A variety of angioplasty procedures and instruments are known. See, e.g., U.S. Pat. Nos. 4,838,269 and 4,794,928 (the disclosures of which are to be incorporated herein by reference). A subject in need of treatment to prevent restenosis (i.e., either during angioplasty or after angioplasty prior to the onset of restenosis) may be treated by applying a time-varying magnetic field to the lumen of the vessel which has been reshaped.

I have found that a 20 minute exposure to an 80 $\mu$T, 60 Hz magnetic field helps protect cells against ionizing radiation (e.g. UV light, x-rays, or gamma rays) applied 1 hour later. Skin tissue under stress due to ultra violet irradiation may be treated by the method of the present invention. My magnetic fields do not induce stress proteins in malignant tissue as effectively as in normal tissue. Thus these fields are useful in protecting normal tissue surrounding tumors when ionizing radiation is used to kill tumor cells. When the tumor and surrounding tissue are exposed first to a magnetic field the result is that a differential sensitivity to the insult of the lethality of the ionizing radiation exists. Thus tumor cells can be destroyed without causing as much damage to surrounding normal tissue. To protect skin tissue under stress due to UV irradiation a magnetic field can be used after exposure to UV to enhance repair and healing of the tissue. The magnetic field can also be applied before exposure to, for example sunlight or other UV sources in order to prevent burning and enhance tanning. Tissues may also be under stress due to chemotherapeutic treatment, as in cancer chemotherapy. My magnetic fields induce only a weak stress response in malignant tissue. Thus cancerous tissue will not be protected against the toxic effects of chemotherapy by the application of my magnetic field while the normal tissue will be protected. In such cases the magnetic field can be applied prior to or after the chemotherapeutic treatment as both a protective and healing agent.

Because the composition of stress proteins induced by my magnetic field is not identical to that induced by heat shock there can be advantages in using a combination of magnetic field followed by a temperature rise to yield greater protection than a heat rise alone can produce. If the magnetic field is applied first then a significantly smaller rise in temperature is needed to induce a heat shock response if this heat shock is applied within 30 minutes to several hours later. For example following a 20 minute exposure to a 4 $\mu$T 60 Hz field the tissue temperature needs to be raised to only 41 degrees C for 20 to 30 minutes to induce a full heat shock response. Without the pre-exposure to the magnetic field the temperature must be raised to 43 degrees C or higher. Thus the pre-exposure to the magnetic field offers a great practical advantage in that the temperature gradients to surrounding tissue is smaller. This is quite useful when one is attempting to use any type of focused heat sources. Examples of this are a focused ultrasonic beam or a magnetic resonance imaging device used to focus energy into a very localized region of tissue. Even if it is desired to induce a heat shock response in a broad unfocused region it is still useful to first "sensitize" the region using my magnetic field and then apply the heat. The synergistic effect of the magnetic field and the elevated temperature is biologically extremely relevant and results in the protection of cells against exposure to cytotoxic conditions.

When skin tissue is taken from one part of the body and grafted on to another part, the probability of a successful graft is greatly increased if, before removing the skin flap our magnetic field is applied. This because the magnetic field induces a stress response to protect the skin tissue from the ischemia taking place after the excision and before revascularisation occurs in the grafted position.

The magnetic field may be applied either concurrently or in combination with other therapeutic agents. For example, the field may be combined with another agent known to help protect cells from acute injury. Such agents include antioxidants or free radical scavengers such as vitamins C and E and superoxide dismutase when the damaging event works through the production of reactive oxygen molecules. The magnetic field may be combined with non-steroidal anti-inflammatory drugs such as indomethacin which are known[21] to sensitize the cell to respond to stimuli known to cause heat shock proteins. When the mechanism of cell damage involves the influx of extracellular calcium, the other agent might be one which reduces the influx of excess calcium ions (e.g., in brain tissue) such as dextrorphan and MK-801. When the mechanism of damage is myocardial infarction, the other agent might be one that removes the blockage of blood flow to the heart muscle, such as tissue plasminogen activator (TPA) and streptokinase.

OPERABILITY OF INVENTIONS

I have confirmed the operability of my inventions by a number of observations and procedures. One observation has been the protective effect of exposure of cells to a 60 Hz magnetic field, preventing much of the deleterious effect of anoxia on cells in vitro. Survival rates of mammalian cell cultures were determined following exposure to a magnetic field and then placed in an anoxic condition. This was done as follows.

a. Three flasks seeded with L929 cells ($1\times10^6$ per 25 cm$^2$ flask) approximately 24 hours (h) previously were used in each experiment. One flask remained in its original incubator to serve as a control The other two were placed in Helmholtz coil exposure systems, one flask in each set of coils. One flask was exposed to a 60 Hz, 10 $\mu$T magnetic field for one hour. The other coil system was not turned on.

b. The two flasks remained in the exposure devices for an additional 3 h, with none of the coils activated. At the end of this time they were transferred to the incubator with the control flask for an additional 1.5 h .

c. Flasks were removed from the incubator (this occurring at 5.5 h following onset of EMF exposure) and the cell culture medium was poured out. For the two flasks to be subjected to anoxia the cells were washed once with 5 ml phosphate buffered saline, once with 5 ml of a balanced salt solution (HBSS) designed for anoxic conditions (composition given below), and given a final change of HBSS. Control cells remained in their original medium.

d. For the two flasks to be subjected to anoxia, argon was flowed through each flask for 3 m to displace the air. The cap of each flask was then tightly sealed, and the flasks were returned to a cell culture incubator for 4 h of anoxic conditions.

e. At the end of the 4 h anoxia period the flasks were removed from the incubator, opened, and the HBSS or culture medium was poured out. Cells were trypsinized to remove them from the growth surface of the flasks, and counts of viable cells were made using trypan blue vital staining. From each flask 50 live cells were pipetted into a 60 mm plastic culture dish with 5 ml of complete cell culture medium (MEM +5% donor calf serum). Five such dishes were prepared from each flask.

HBSS contains the following; 1.3 mM $CaCl_2$, 5.0 mM KCl, 0.3 mM $KH_2PO_4$, 0.5 mM $MgCl_2$, 0.4 mM $MgSO_4$, 69 mM NaCl, 4.0 mM $NaHCO_3$, 0.3 mM $Na_2HPO_4$.

f. Dishes were placed in a $CO_2$-injection, cell culture incubator and maintained for approximately 11 days to allow cells to settle, attach, and proliferate sufficiently to produce colonies. The culture medium was then removed from each dish, and the dish was fixed using absolute methanol. Cells were stained with 0.5% methylene blue and, using a phase contrast microscope to impart additional contrast, counts were made of stained colonies with more than 20 cells.

TABLE 1

Comparison of survival rates for cells with and without previous exposure to 60 Hz magnetic fields and which were subsequently placed under anoxic conditions

| | Percentage of Colonies Which Survived | |
|---|---|---|
| | Anoxia Alone | Anoxia + EMF |
| Run #1 | 39 | 79 |
| Run #2 | 41 | 76 |
| Run #3 | 48 | 76 |

It can be seen in Table 1 that only approximately 40% of the colonies survived when placed in dishes under anoxic condition for 4 hours. However in those dishes which had previously been exposed to a magnetic field for 1 hour the survival rate was almost 80%. The results of this experiment clearly demonstrate that cross protection has occurred. Thus I see that for the first time it has been shown that exposure to a time varying magnetic field can confer protection against anoxia in biological cells.

In a second series of experiments chick embryos which had been incubated for approximately 94 hours were exposed to an 8 $\mu$T, 60 Hz magnetic field for 40 minutes.

After a 40 minute delay the embryos were placed in an anoxic condition by putting them in a plastic freezer bag and allowing argon to flow through the bag for approximately one minute. The bag was then sealed. After approximately 80 minutes the embryo hearts were visually observed. The results are presented in Table 2. It can be seen that the pre-exposure to a magnetic field significantly inhibited the effects of the anoxia. Similar results can be obtained at other frequencies as high as 6000 Hz and above and at field exposure times of only 20 minutes or less.

TABLE 2

Comparison of chick embryos with and without previous exposure to magnetic fields which were placed under anoxic conditions for approximately 80 minutes

| EMF exposure conditions | Percentage of Hearts Beating (after 80 minutes) | |
|---|---|---|
| | Anoxia alone | Anoxia + EMF |
| 40 min/8 µT | 25% (n = 5) | 80% (n = 5) |
| 20 min/10 µT | 14% (n = 7) | 100% (n = 7) | n = the number of different runs for a given exposure condition.

In another series of experiments the threshold magnetic field strength for causing beneficial effects was determined. In these experiments embryos which had incubated for 94 hours were then exposed for 20 minutes to 60 Hz magnetic fields ranging from 0 to 8 µT. They were then put into anoxic conditions for approximately 90 minutes until about 40% of the controls survived. The results are shown in FIG. 1 of the drawings which are a part of this application. FIG. 1 shows the effect of changing the rms amplitude of a 60 Hz magnetic field on the survival rate of chick embroyos placed under anoxic conditions. Control values were approximately 37.5%. Significant improvement of survival rates (relative to control) occurred only for fields whose rms amplitude was above about 4 µT. Above 4 µT the percent surviving in the exposed group is almost twice that of the controls. It can be seen from FIG. 1 that below 4 µT the effectiveness of the magnetic field begins falling rapidly. At 2 µT and below no beneficial effect is observed. The percent surviving was equal to that in the control group. Very similar results were obtained at 6000 Hz.

Time is truly of the essence in the treatment of ischemia. The sooner one can stimulate the endogenous protective mechanism to respond the more effective is their protective action. For example it takes several hours to stimulate a significant stress response if one uses of cadmium (a typical toxic drug under consideration) or amino acid analogs. This is a serious limitation on the efficacy and practicality of this approach. The use of electromagnetic fields would have a great advantage over hyperthermia treatments or drug treatments such as the injection of cadmium or amino acid analogs.

In the research on thermotolerance and cross protection described above the treatment always preceded the event which it was trying to protect against (e.g. ischemia or lethal rise in temperature). It would be of enormous practical importance if the treatment modality could be used after the onset of an ischemic event. To test the efficacy of applying an electromagnetic field after the start of an ischemic event the following procedures were performed. In a series of experiments chick embryos which had been incubated for approximately 94 hours were exposed to an 8 µT, 60 Hz field for 20 minutes. The exposure in one group started simultaneously with the start of anoxia. In another group the exposure started 20 minutes after the start of anoxia. The results are presented in Table 3. It can be seen that significant improvement in survival rates were observed even when the exposure was begun shortly after the start of anoxia. This means that if a device for applying the magnetic field was available in the home, office or other place a person experiencing symptoms of a heart attack or stroke would be able to self administer the field using embodiments described below. Of course to be of general use the device must not only be simple to use but must be very inexpensive so that it can be available to the large part of the population at risk of heart attack or stroke. My inventions satisfy these conditions.

TABLE 3

Comparison of chick embryos with and without a 20 minute exposure to an 8 µT, 60 Hz magnetic fields and which were placed under anoxic conditions for approximately 90 minutes

| EMF Exposure Conditions | Percentage of Hearts Beating (after 90 minutes of anoxia) | |
|---|---|---|
| | Anoxia alone | Anoxia + EMF |
| Starting simultaneously with anoxic condition. | 20% (n = 5) | 60% (n = 4) |
| Starting 20 minutes after anoxic condition is applied. | 33% (n = 18) | 62% (n = 21) | n = the number of embryos for a given exposure condition.

DESCRIPTIONS OF PREFERRED EMBODIMENTS OF APPARATUS

In its simplest form a protecting apparatus for carrying out my methods consists of a periodic signal generator operating in the range of 10 to 30,000 Hz, and a coil through which current from the signal generator is made to flow. The flow of current through the coil produces the time varying magnetic field necessary to induce the natural biological defense mechanisms. Both the signal generator and the coil can be implemented in a number of ways. Following are several sample implementations of each of these components.

SIGNAL GENERATORS

EXAMPLE 1

AC Powered, Transformer Coupled, Power Frequency Generator

If ac power is available the protective signal generator can be implemented as a simple voltage transformer. The transformer could be designed with a secondary winding of voltage and resistance suitable to drive the coil directly at the required current level. A generator of this type would be very economical, consisting solely of an ac/ac wall plug-in transformer with a suitable means to connect to the field producing coil.

EXAMPLE 2

Ac Powered, Transformer Coupled, Periodic Signal Generator

An ac source can also be used to implement the protection signal generator as a periodic ELF signal of shape and frequency other than power line fields. In this case the signal generator would generally consist of a dc source, a circuit to make the ELF periodic signal of choice, and a circuit to couple the periodic signal to the field producing coil.

For safety reasons a transformer coupled dc source would generally be recommended. A dc source of this type is easily constructed by standard methods using a suitably rated transformer, a half wave or full wave rectifier, a charging capacitor, and a voltage regulator such as one of the LM78XX made by National Semiconductor of Santa Clara, Calif.

As noted earlier, suitable periodic signals include sinusoidal waves, triangular waves, square waves, pulse trains, and other periodic signals of frequency within the appropriate range. Sinusoidal, triangular, and square wave generators can be designed using either suitably interconnected operational amplifiers or specialized wave generating integrated circuits, such as the ICL8038 made by Harris Semiconductor of Melbourne, Fla. Alternatively, any type of signal can be generated with a microprocessor or a microcontroller and the appropriate software control. While the first method can be more economical, the second would readily permit for the generation of more complex exposure patterns, for instance periodic re-application of the protective field.

An additional circuit is generally needed to allow driving the field generating coil at the appropriate current level. The configuration of this circuit would depend on the type of periodic signal to be used, and the coil design and construction. A transistor current amplifier could be used when the periodic signal is a pulsing dc signal. An audio power amplifier design would be more suitable when the periodic signal is an ac signal. Suitable audio power amplifiers can be made using discrete components, that is, transistors or operational amplifiers. Alternatively commercially available power amplifier integrated circuits could be used such as the LM383, the LM384, or the LM386 manufactured by National Semiconductor of Santa Clara, Calif.

EXAMPLE 3

Battery Driven Periodic Signal Generator

Since portability can be an important feature, the signal generator can be easily designed as a battery operated device. In this case the generator would consist of a circuit to make the periodic signal of choice, and a circuit to couple the periodic signal to the field producing coil. Both of these components can be implemented in the same manner as described in the previous example. The battery operated generator can be used in conjunction with a suitable coil to make a protective device which can be worn by an individual at all times. For this application it would be advantageous to fit the generator into a small package. This can be achieved using surface mount components and thin high capacity batteries, for instance, batteries of the type used in cellular phones. Such a device could be made into a unit that could, for instance, be worn on a belt, attached to a pocket, or hung on a chain around the neck. Attachment to the coil would be via a physical paired wire connection.

FIELD GENERATING COILS

In general the EMF generating coil should consists of one or more multi-turn coils of conducting material, for instance wire, arranged and connected in such a fashion that when electric current flows through them an appropriate magnetic field is produced within the tissue, organ, or other biological entity to be treated with the electromagnetic fields prescribed in the present invention. The coils can be configured in a number of ways which can be selected depending on the intended application. Some examples follow.

EXAMPLE 1

Dual Coil Configuration

Figure 2:
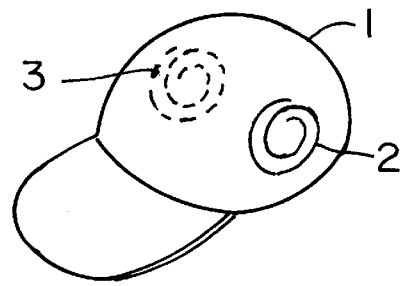
FIG. 2 shows field generating coils on opposite sides of a hat worn by a patient.
Figure 3:
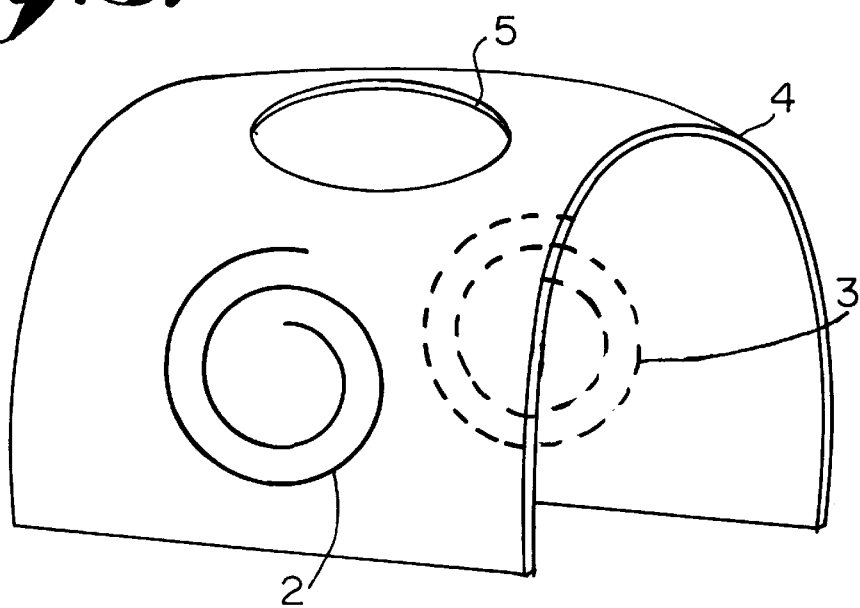
FIG. 3 shows field generating coils on the front and rear of a vest worn by a patient.
Figure 4:
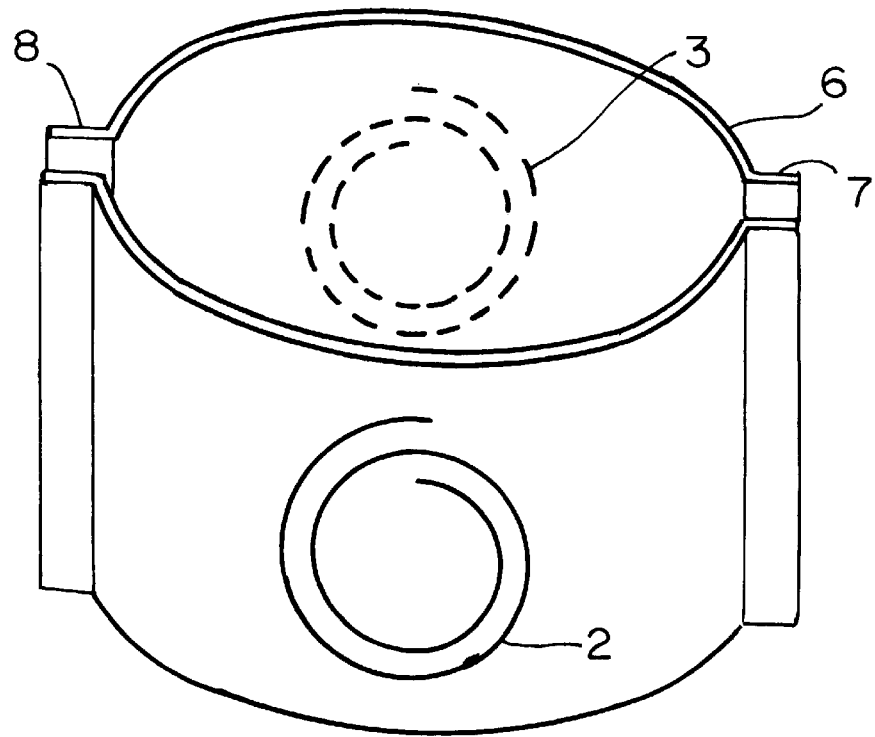
FIG. 4 shows an alternative form of vest, secured by Velcro straps.

If two coils are placed parallel to one another and separated by a distance equal to their radius (radius rule), and with currents carried in the coils in directions to cause additive fields, a substantially uniform magnetic field can be generated in the region between the coils. This type of dual coil, called a Helmholtz coil, can allow fairly uniform exposure of large regions of the body. For instance, if the target is the brain the coils could be located on opposite sides of a hat worn by the patient. In FIG. 2 reference character 1 points to a cap to be worn on the head of a human patient. A multiturn coil 2 of electrically conductive wire is placed on one side of the cap, and a complementary Helmholtz coil 3 placed on the opposite side. The pair of coils could be on the front and rear, or on any other desired axis across the cap. If the target is the heart, the coils could be located on the front and back sides of a vest which can be slipped over the head of patient and secured to his/her torso with side straps. In FIG. 3 a vest 4 is illustrated to be worn over the chest and back of a human patient, an opening 5 being provided for slipping down over the patient's head. Helmholtz coils 2 and 3 are shown on the front and rear panels of the vest. Alternatively the coils could be installed side by side, with suitable distance in between, on a flat cloth band with Velcro securing straps. The band could be wrapped around the torso in such a manner that the coils rest on the front and back. FIG. 4 shows another form of vest 6 which is wrapped around the patient's torso and secured by Velcro bands 7 and 8. In this way the coils may be on any axis across the patient's torso. A similar band could also be used for the head, but an opening around the face would be needed for the comfort of the patient. If the size of hats, etc., does not permit the radius rule to apply, other distances may be used, preferably as near to the radius rule as possible.

EXAMPLE 2

Single Coil

Figure 5:
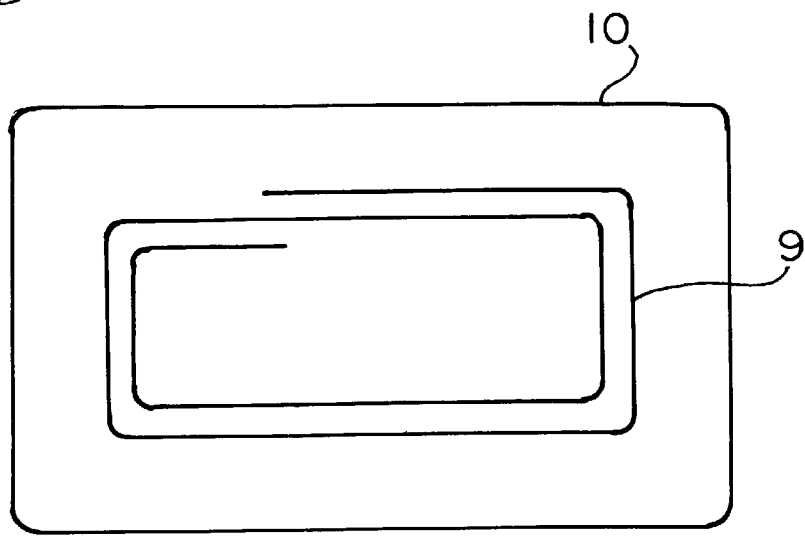
FIG. 5 shows a single field generating coil within a pillow or pad.

The use of a pair of coils is advantageous because it can allow for relatively uniform exposure of a region of interest. However, a single coil can also be used if appropriately positioned. For instance the coil can be placed within a pillow or pad. FIG. 5 shows a single coil 9 placed in a pillow or pad 10 on which the patient's head may rest while asleep. of dimensions such that when a patient rest his/her head on it, the head region is subjected to the appropriate field which can cause the desired protection effect. One example of a single coil embodiment consists a multi-turn rectangular coil measuring 26"×20", embedded within a standard size pillow. This "pillow" applicator can allow for delivery of the treatment with minimal disturbance to the patient. If firm pillows are used the center of the head should be located an average of 7" away from the plane of the coil. The magnetic field generated by this coil can be calculated by adding up all contributions from infinitesimal current elements along the entire loop. For the purpose of determining the range of exposure levels from this coil I assume that the sensitive regions of the head are located within a volume enclosed by a 22"×16"×4" parallelepiped resting on a plane 5" above the plane of the coil and centered directly over the coil. The magnetic field inside this volume varies within ±45% of the average of the maximum and minimum fields. For instance, if the axial field on the plane of the coil is 20 mG, the field variation inside the specified volume would be between approximately 4 mG and 13 mG.

Figure 6A:
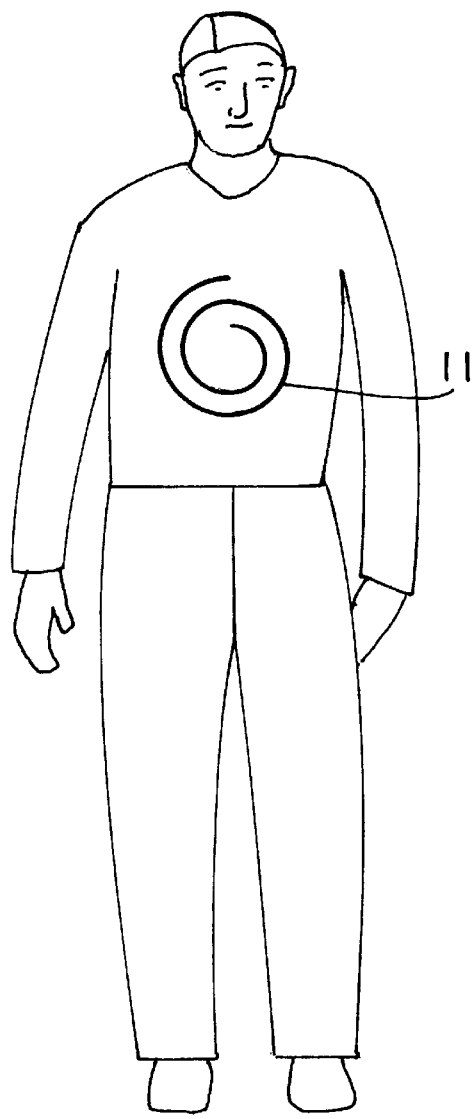
FIG. 6a shows a front view of body clothing with a field generating coil there on in the form of an electrically conductive strip.
Figure 6B:
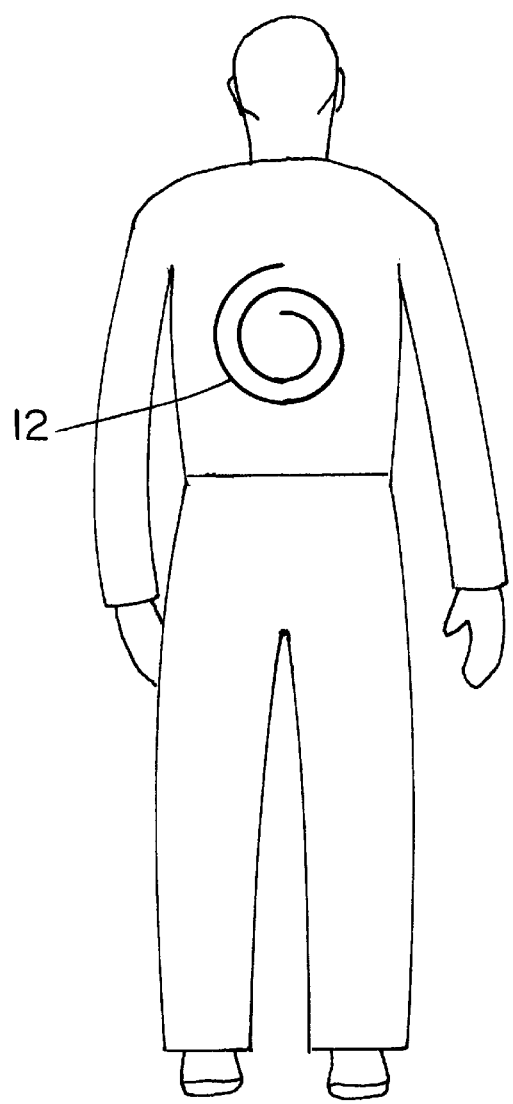
FIG. 6b shows a coil as in FIG. 5 but on the back of the clothing.

Either single, dual or other multi coil applicators can be designed as part of any article of clothing using, for instance, traces made with conductive paint. With this approach the magnetic field can be directed to any part of the body using any number of appropriately positioned traces. Body suits would be convenient garments for this purpose. In FIG. 6a a body suit or garment is shown on which a coil 11 is in the form of a conductive trace affixed to the suit. FIG. 6b shows a second coil 12 on the rear of the suit. The coils may be placed at any elevation on any axis across the torso of the patient. If the organ to be protected is in the head, any type of hat or cap could be used.

Either the dual coil band applicator or the single coil applicator can be effectively used to pre-treat any tissue/organ region prior to a surgical procedure.

DEVICES OF APPARATUS OF INCREASED COMPLEXITY

A device with built-in monitoring to detect threatening conditions could be designed for high risk patients. This device would be worn at all times and would be activated immediately when needed. The conditions to be met for activation have to be determined using clinical data. This device could be of particular interest for patients with high risk of heart attacks, brain strokes or other similar conditions which are characterized by oxygen deprivation. Transmission between the monitoring unit and the protection signal generator could be achieved via a wireless link using standard methods. There are numerous commercially available devices available to monitor biological activity. Some of these are worn in the fashion of a wrist watch. The implementation of the proposed protection device with monitoring would require the integration of a signal transmitter into the monitoring module and a signal receiver into the protection signal generation module. Suitable transmitter/receiver modules are commercially available.

FOOTNOTED CITATIONS

1. American Heart Association, 1990. Heart Facts. American Association National Center. Dallas pg. 1
2. Bonventre JV, 1988. Mediators of ischemic renal injury. Ann Rev Med 39, 531–544.
3. Ananthan J, Goldberg AL, Voelmy R, 1986. Abnormal proteins serve as eukaryotic stress signals and trigger the activation of heat shocks genes. Science 232: 522:544
4. Mestril R, Dillmann WH, 1995. Heat shock proteins and protection against myocardial ischemia. J Mol Cardiol 27, 45–52.
5. Donnelly TJ, Sievers RE, Vissern FLJ, Welch WJ, Wolfe CL, 1992. Heat shock protein induction in rat hearts. Circulation 85: 769–778.
6. Walker DM, Pasini E, Kucukogolu S, Lin JJC, Feramisco JR, 1983. Heat stress limits infarct size in the isolated perfused rabbit hears. Cardiovasc Res 27: 962–967
7. Li GC, Mak JY, 1985 Induction of heat shock protein synthesis in murine tumors during the development of thermotolerance. Cancer Res 45:3816–3824.
8. Iwaki K, Chi SH, Dillmann WH, Mestril, R. 1993. Induction of HSP70 in cultured rat neonatal cardiomyocytes by hypoxia and metabolic stress. Circulation 87: 2023–2032
9. Hutter MM,Sievers RE, Barbosa V, Wolfe CL, 1994. Heat shock protein induction in rat hearts: a direct correlation between the amount of heat shock protein induced and the degree of myocardial protection. Circulation 89: 355–360
10. Mestril RM, Chi SH Sayen MR, O'Reilly K, Dillman WH 1994 Expression of inducible stress protein in rat heart myogenic cells confers protection against stimulated ischemia induced injury. J. Clin Inves 93:759–769
11. Heads RJ, Yellon DM, Latchman DS, 1995. Differential cytoprotection against heat stress or hypoxia following expression of specific protein genes in myogenic cells. J. Mol Cell Cardio. 27, 1669–1678
12. Joannidis M, Cantley LG, Spokes K, Medina R, Pullman J, Rosen, Epstein FH, 1995. Induction of heat shock proteins does not prevent renal tubular injury following ischemia. Kidney Int. 47(6): 1752–1759
13. Marber M, Mestril R, Chi SH, Sayen MR et al. 1995. Overexpression of the rat inducible 70-kD heat stress protein in a transgenic mouse increases the resistance of the heart to ischemic injury. J Clin Invest. 95 1446–1456
14. McLeod KJ, Lee RC, Ehrlich HP, 1987. Frequency dependence of electric field modulation of fibroblast protein synthesis. Science June 12; 236(4807): 1465–1469
15. Goodman R and Henderson A, 1987. Patterns of transcription and translation in cells exposed to EM fields: A review. Mechanistic Approaches to Interactions of Electric and Electromagnetic Fields with Living Systems, Ed Martin Blank and Eugene Pindl, Plenum Publishing Corp, 1987 pp 217–230
16. Goodman R, Henderson AS 1988. Exposure of salivary glands cells to low frequency electromagnetic fields alters polypeptide synthesis. Proc Natl Acad Sci USA June; 85 (11):3928–3932
17. Blank, M, Goodman R 1988. An electrochemical model for the stimulation of biosynthesis by external electric fields. Bioelectrochem and Bioenerg. 19: 569–580
18. Edginton SM, 1995 Therapeutic applications of Heat Shock Proteins, Biotechnology 13: 1442–1444
19. Sedlak BJ, 1996, Heat shock proteins finding a broad range of clinical uses and applications. Genetic Eng. News, February, p 6.
20. Albertini A, Noera G, Pierangeli A., Zucchini P, and Cadossi R, 1991 Effect of Low-frequency pulsed electromagnetic fields on experimental myocardial infarcts in rats, electromagnetics in Biology and Medicine, San Francisco Press Inc. ed. CT Brighton and SR Pollack pp 187–189.
21. Lee BS, Chen J, Angelidis C, Jurivich DA, Morimoto RI, 1995 Pharmacological modulation of heat chock factor 1 by anti-inflammatory drugs results in protection against stress-induced cellular damage. Proc.Nttl.Acad.Sci.USA Aug. 1, 1992(16):7202–11

CONCLUSION

Given the foregoing descriptive material those of skill in the art will visualize modifications of the inventions. Therefore, the scope of the inventions is to be determined from the appended claims.

I claim:

1. A method of combating irreversible injury or mortality in a biological cell, tissue or organ, caused by an adverse condition including, without limitation, lack of oxygen, ischemia/reperfusion, hypoglycemia, altered metabolic or electrolyte environment, breakdown of cell membrane functions, ionizing radiation, oxidative stress, and toxic substances, which method includes induction of stress proteins by exposure of the cell, tissue or organ to a time varying field selected from a group of fields consisting of electric, magnetic and electromagnetic fields, wherein the time of beginning the exposure falls within a period extending from approximately 2 hours before the start of the adverse condition to at least 20 minutes prior to the completion of irreversible injury or mortality.

2. A method as in claim 1 wherein the duration of the exposure is less than approximately 1 hour.

3. A method as in claim 1 or 2 wherein the cell, tissue or organ is re-exposed to one of the fields starting 1 to 2 hours after the end of the first exposure.

4. A method as in claim 3 wherein the duration of the second exposure is less than approximately 1 hour.

* * * * *

UNITED STATES PATENT AND TRADEMARK OFFICE
CERTIFICATE OF CORRECTION

PATENT : 5,968,527
DATED : October 19, 1999
INVENTOR(S) : Theodore A. Litovitz et al It is certified that error appears in the above-identified patent and that said Letters Patent is hereby corrected as shown below:

In column 18, lines 57-58, please delete "to at least 20 minutes prior to the completion of irreversible injury or mortality".

Signed and Sealed this

Fifth Day of September, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,968,527  
DATED : October 19, 1999  
INVENTOR(S) : Theodore A. Litovitz It is certified that error appears in the above-identified patent and that said Letters Patent is hereby corrected as shown below:

Column 1,  
Line 3, please insert the following:

-- GOVERNMENT INTEREST STATEMENT

This invention is made with government support under contract number 5R01ES6872-3, awarded by the National Institute of Health (National Institute of Environmental Health Sciences). The government may have certain rights in this invention. --

Signed and Sealed this

Sixth Day of January, 2004

JAMES E. ROGAN  
*Director of the United States Patent and Trademark Office*